(12) United States Patent
George et al.

(10) Patent No.: US 8,096,956 B2
(45) Date of Patent: Jan. 17, 2012

(54) MULTIFUNCTIONAL BIOPSY INSTRUMENT

(75) Inventors: Samuel George, Surrey (GB); Christopher Richardson, London (GB)

(73) Assignees: Samuel George, Surrey, England (GB); Christopher Richardson, London, England (GB)

( * ) Notice: Subject to any disclaimer, the term of this patent is extended or adjusted under 35 U.S.C. 154(b) by 232 days.

(21) Appl. No.: 12/440,348

(22) PCT Filed: Sep. 5, 2007

(86) PCT No.: PCT/GB2007/003332
§ 371 (c)(1), (2), (4) Date: Apr. 17, 2009

(87) PCT Pub. No.: WO2008/029120
PCT Pub. Date: Mar. 13, 2008

(65) Prior Publication Data
US 2009/0318830 A1    Dec. 24, 2009

(30) Foreign Application Priority Data
Sep. 8, 2006 (GB) .................................. 0617736.4

(51) Int. Cl.
*A61B 10/00* (2006.01)
(52) U.S. Cl. ........................................ 600/564; 600/562
(58) Field of Classification Search ........... 600/562–572
See application file for complete search history.

(56) References Cited

U.S. PATENT DOCUMENTS

| 4,763,669 A | * | 8/1988 | Jaeger | 600/564 |
| 5,471,992 A | * | 12/1995 | Banik et al. | 600/564 |
| 2005/0043758 A1 | * | 2/2005 | Golden et al. | 606/206 |

* cited by examiner

*Primary Examiner* — Jeffrey G Hoekstra
(74) *Attorney, Agent, or Firm* — Dinsmore & Shohl LLP

(57) ABSTRACT

A biopsy instrument comprises a cutting head having first and second co-operable jaws movable with respect to a support between open and closed states, and a jaw drive for moving one or both of the jaws into the closed state to take a biopsy sample in response to an actuating input from a user. The jaw drive is user-adjustable between first and second cutting modes differentiated by the response of the jaws to the actuating input. In the first cutting mode, both jaws may move equi-angularly with respect to the support between the open and closed states; in the second cutting mode, one jaw may remain stationary with respect to the support such that only the other jaw moves between the open and closed states.

60 Claims, 8 Drawing Sheets

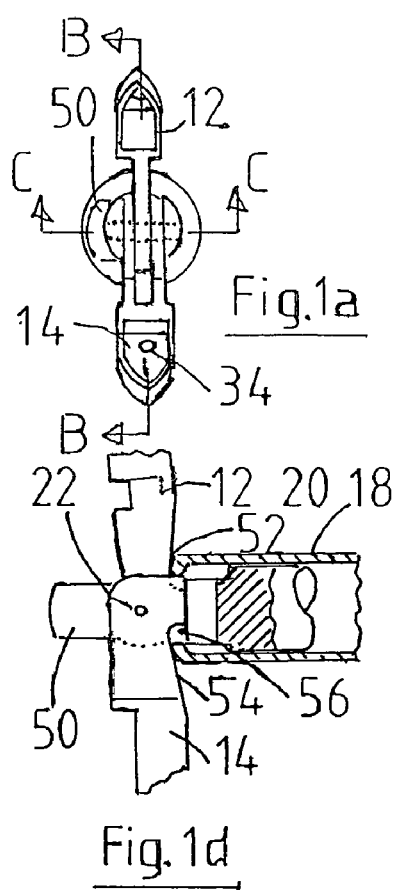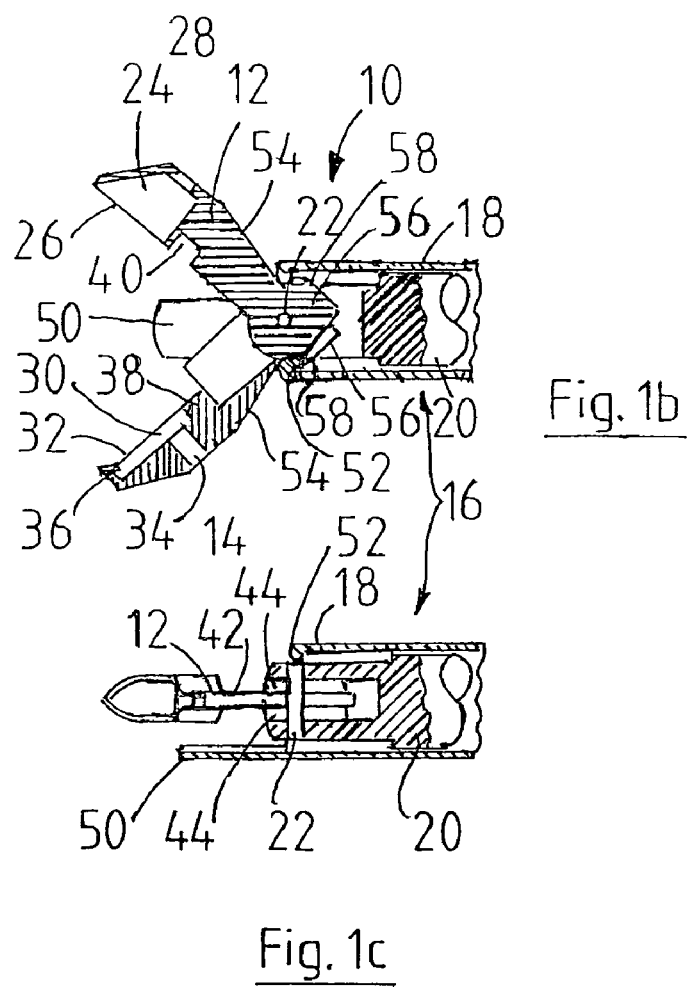

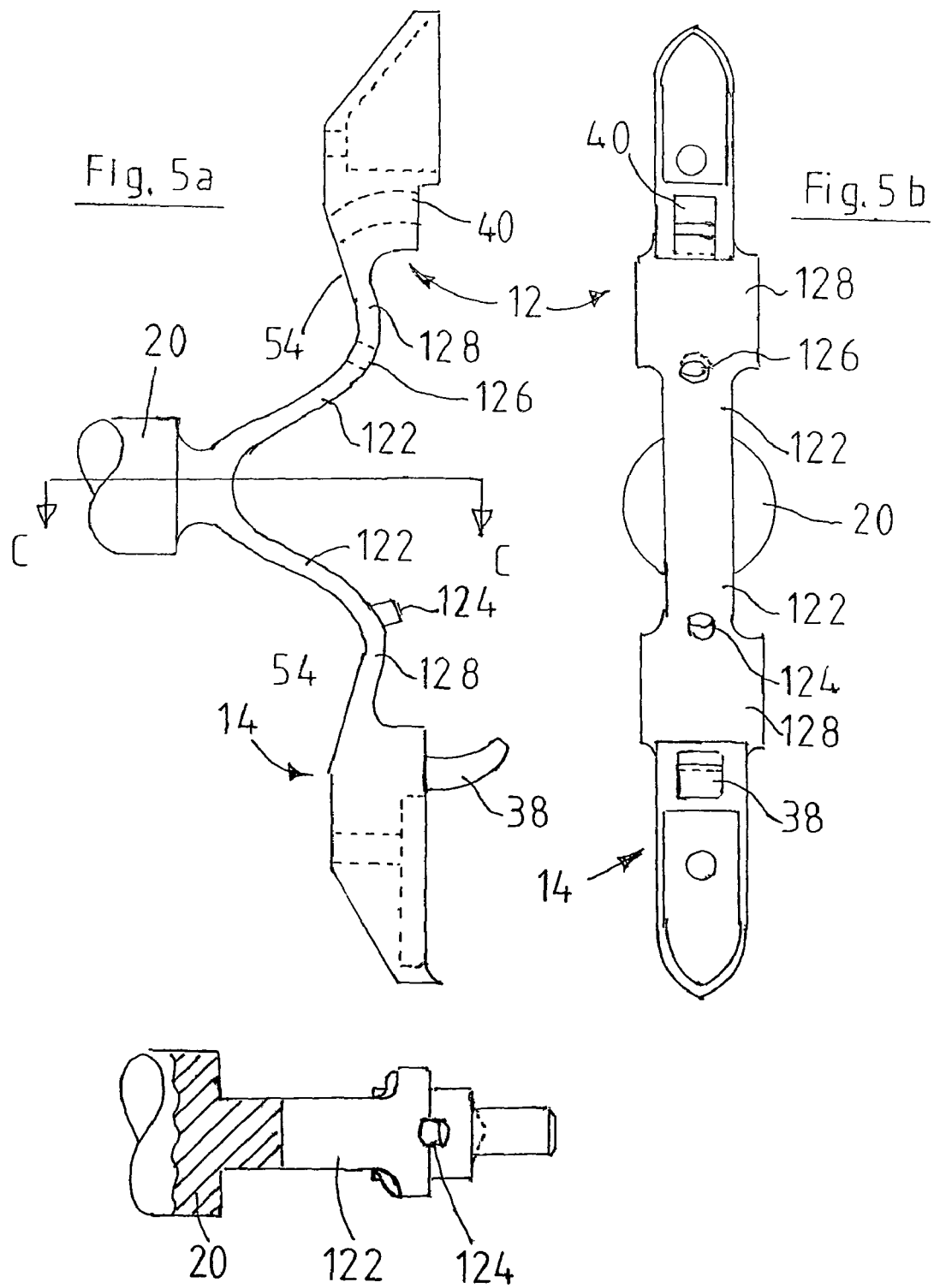

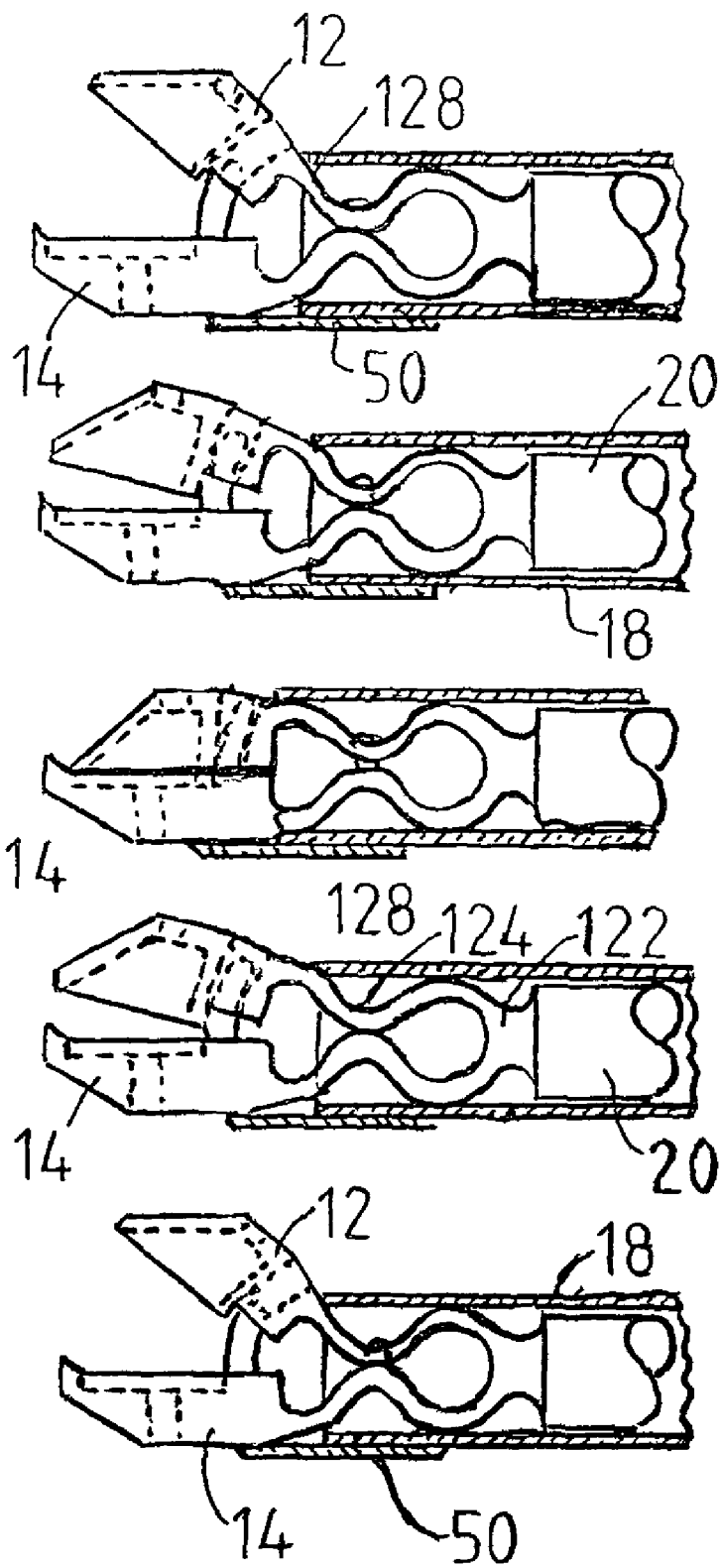

MULTIFUNCTIONAL BIOPSY INSTRUMENT

This invention relates to a biopsy instrument suitable for sampling various body tissues, for example from the uterine cervix following a colposcopy procedure.

Whilst the invention will be described herein in the context of sampling tissues from the uterine cervix, the instrument of the invention may be used to sample other tissues, such as ovarian tissues.

Cancer of the uterine cervix, or cervical cancer, usually progresses slowly over an extended period from the first appearance of pre-cancerous abnormalities. Before malignant cells are found, the tissues of the cervix go through changes in which abnormal cells begin to appear, initially on the epithelial tissue on the surface of the ectocervix. This pre-cancerous condition is known as dysplasia or cervical intraepithelial neoplasia (CIN).

CIN is a lesion of abnormal cells typically associated with the Human Papilloma Virus (HPV). When HPV is contracted, it most commonly infects the cells of the transformation zone where squamous cells from the ectocervix meet columnar cells characteristic of the endocervical canal. The transformation zone is apparent at the surface of the cervix as a squamocolumnar junction that lies on the convex annular lip of the cervix encircling the opening at the external end of the endocervical canal, which opening is known as the external os.

The transformation zone is where the cells of the cervix actively divide and grow and where cancers most often start. When HPV infects the cells and then becomes active, abnormal cells begin to be produced in the transformation zone and a CIN lesion develops in the epithelial tissue at the surface of the cervix, usually starting at the squamocolumnar junction.

CIN does not directly infer cancer but refers to a spectrum of abnormality ranging from mild dysplasia, that may regress without intervention, to severe dysplasia that may extend to carcinoma-in-situ, the cancer initially being localised to the intraepithelial tissue or superficial layer of the ectocervix. If left untreated, the cancer cells will start to grow and spread more deeply into the cervix and to surrounding areas, necessitating hysterectomy at best and, of course, threatening the patient's life.

If left untreated, around 30% to 50% of CIN conditions may progress to invasive cancer. However, with effective screening, many patients will entirely avoid cervical cancer if they can benefit from preventative intervention. Even for those who do not, there is a good prognosis if the cancer is detected and treated early enough. Clearly, detection and treatment of CIN is essential to avoid the possible development and progression of cervical cancer.

Screening for CIN starts with regular smear testing. Women with smears showing a significant risk of developing cervical cancer will be referred for colposcopy, which involves detailed visual inspection of the cervix. Commonly, the colposcopy procedure will conclude by taking one or more biopsies of cervical tissue.

Cervical biopsies are usually taken with biopsy forceps. Biopsy forceps have co-operable distal jaws that engage and cut a small portion of cervical tissue, excising and retaining a tissue sample between the jaws for subsequent analysis. The jaws may be operated by long scissor-like proximal handles pivoting about an axis close to the distal end of the instrument. Alternatively, the jaws may be operated by a proximal trigger mechanism acting on the jaws via a rod extending through an elongate shaft. Such instruments are also known as biopsy punches in view of their punch-like cutting action. In each case, the handles or the shaft are long enough to extend the length of the vagina and moreover to give clearance for the physician's fingers to operate the jaws using the handles or the trigger, without unnecessarily touching the patient.

Numerous jaw configurations are used in cervical biopsy instruments, such as those of the Schubert and Tischler instruments. The beak-like jaws generally carry overlapping scissor-action or punch-action blades, at least one of which defines a pocket or basket for retaining the tissue sample. Typically, the blades of one jaw fit within the surrounding blades of the other jaw. Side portions of the blades may converge distally to a point or may be parallel, joining in a rounded distal blade portion. The distal extremities of the blades may have one or more hooked teeth to engage the cervical tissue as the jaws close, so as to prevent the tissue from slipping out of the bite of the jaws before the sample has been cut fully.

The size, shape and position of the external os, the ectocervix and the squamocolumnar junction vary widely with age, hormonal state, and whether the woman has had a vaginal birth. For example, the squamocolumnar junction is typically irregular and may lie at various distances from the external os around the convex annular lip of the cervix. This presents challenges in designing the jaws of cervical biopsy instruments, and explains the numerous jaw configurations that are in use.

The jaws of many cervical biopsy instruments are of substantially different lengths, one jaw extending distally beyond the other to a considerable extent. Moreover, the bite direction is often offset with respect to the central longitudinal axis of the instrument so that when open, the angle between the jaws is bisected by a line that is offset by perhaps 30° with respect to that axis. For example, the longer jaw may be fixed in alignment with the central longitudinal axis and the shorter jaw, when open, may lie at approximately 60° with respect to the shorter jaw.

These jaw configurations suit the most common situation in which the squamocolumnar junction lies close to the external os, on the inwardly-facing portion of the convex annular lip of the cervix that surrounds the external os. In use during a biopsy procedure, the tip of the longer jaw aligns with the external os to extend beyond the front face of the lip of the cervix, where it can engage the inwardly-facing lip portion around or within the external os. The tip of the shorter jaw simultaneously engages the front face of the lip, proximally and outwardly with respect to the tip of the longer jaw. Where the squamocolumnar junction lies close to the external os, this embraces the junction between the open jaws, and so helps to ensure that tissue from the transformation zone is excised as the jaws are closed.

In some patients, however, the squamocolumnar junction lies further away from the external os, on the front face of the lip of the cervix that surrounds the external os. That part of the cervix is more difficult to grip for the purpose of taking a biopsy. Specifically, where the jaws of a biopsy instrument are of substantially different lengths such that one jaw extends distally beyond the other to a considerable extent, the longer jaw tends to push the cervix away from the shorter jaw before the shorter jaw can engage the cervical tissue. This applies particularly when the longer jaw is fixed in alignment with the central longitudinal axis of the instrument such that the bite direction is offset. Such instruments are practically useless for the purpose of sampling cervical tissue from the transformation zone where the squamocolumnar junction lies substantially away from the external os. Instead, it is necessary in that situation to use a different biopsy instrument whose jaws extend distally to substantially the same extent, and which both pivot with respect to the central longitudinal axis of the instrument such that the bite direction is not significantly offset from that axis.

A physician cannot know the position of the squamocolumnar junction until a colposcopy procedure is underway and so cannot, with certainty, select a suitable biopsy instrument before the procedure. A physician may initially choose an instrument with an offset bite on the assumption that the squamocolumnar junction will lie close to the external os, but may then have to choose a different instrument upon finding that the squamocolumnar junction in fact lies further away from the external os. Some trial and error may be necessary before selecting a suitable instrument, particularly as multiple biopsies may be needed from different locations around the irregular squamocolumnar junction. All this prolongs the procedure to the patient's discomfort, and reduces the chance of obtaining effective biopsy results. Also, the use of multiple biopsy instruments is inefficient in terms of the cost of purchase and, if the instruments are not disposable, of repeated sterilisation.

It is against this background that the present invention has been made. The invention resides in a biopsy instrument that may be reconfigured to cut efficiently in at least two different modes, each with a respectively different bite direction.

In one sense, the invention may therefore be expressed as a biopsy instrument comprising:
  a cutting head having first and second co-operable jaws movable with respect to a support between open and closed states; and
  a jaw drive for moving one or both of the jaws into the closed state to take a biopsy sample in response to an actuating input from a user;
wherein the jaw drive is user-adjustable between first and second cutting modes differentiated by the response of the jaws to the actuating input.

In the embodiments to be described, the first and second cutting modes are differentiated by the bite direction of the jaws with respect to a central longitudinal axis of the instrument. The bite direction may be defined as the centreline between the open jaws. For example, in the first cutting mode, both jaws may move with respect to the support between the open and closed states; preferably in that mode, both jaws move substantially equi-angularly with respect to the support. Thus, in the first cutting mode, the bite direction may be substantially aligned with the central longitudinal axis of the instrument. Conversely, in the second cutting mode, one jaw moves more than the other jaw with respect to the support between the open and closed states; preferably one jaw is substantially fixed with respect to the support and the other jaw moves between the open and closed states. Thus, in the second cutting mode, the bite direction is substantially offset from the central longitudinal axis of the instrument.

The jaws are suitably hinged to the support, for example by being attached to the support by a common pivot although different pivot axes are possible. In a variant suitable for moulding, the jaws may be integrally formed with the support via resilient leaves, in which case the leaves may be bent to define a fulcrum, at which the leaves may be attached to each other, and a locating formation that centres the fulcrum with respect to a central longitudinal axis of the instrument.

The support may, for example, be a rod extending proximally from the cutting head, and the jaw drive may be a sleeve movable around the rod. For example, the jaw drive preferably comprises a sleeve that is movable distally with respect to the support to bear against at least one of the jaws, thereby to drive the closing movement of that jaw between the open and closed states. For this purpose, each jaw preferably has a proximally-tapering wedge face against which the sleeve bears when driving closing movement of that jaw between the open and closed states.

In one of the preferred embodiments to be described, the sleeve has an inwardly-extending flange that, when moving distally, bears against at least one of the jaws to drive closing movement of that jaw between the open and closed states. In that case, each jaw preferably has a proximal lug and the flange of the sleeve bears against the lug of at least one of the jaws when moving proximally with respect to the support in a return stroke. In this way, the flange drives opening movement of that jaw between the closed and open states. It is also possible for the proximal lugs of the jaws to co-operate, when closed, to define outwardly-facing parallel flat faces that lie parallel to the inner wall of the sleeve to centre the support within the sleeve.

In the broadest concept of the invention, it is not essential that opening of the jaws is positively driven by the jaw drive. For example, the jaws may be biased by springs or by inherent resilience to assume the open state when released by the jaw drive.

Elegantly, adjustment between the first and second cutting modes may be effected simply by relative angular movement between the sleeve and the support. In that case, if the sleeve has an inwardly-extending flange, the flange is preferably interrupted by a gap that is brought into alignment with one of the jaws in the second cutting mode.

The sleeve may have a jaw-supporting formation that is disengaged from the jaws in the first cutting mode to allow both jaws to move relative to the support and that is engaged with one of the jaws in the second cutting mode to restrain the movement of that jaw relative to the support. For example, the jaw-supporting formation may be a distal extension of the sleeve extending partially around the circumference of the sleeve. Where adjustment between the first and second cutting modes is effected by relative angular movement between the sleeve and the support, the jaw-supporting formation is preferably brought into alignment with one of the jaws in the second cutting mode.

To maintain alignment between the jaws, the jaws advantageously have opposed co-operable alignment formations that mate with each other as the jaws close. It is also preferred that one jaw has a tongue that slides between cheeks of the other jaw.

The actuating input is suitably provided by an actuating mechanism, such as a trigger mechanism, at a proximal end of the instrument. Advantageously, the cutting head is removable from the actuating mechanism such that the actuating mechanism can be re-used with a fresh cutting head. Indeed, the cutting head may be connected to the actuating mechanism by a shaft that comprises the sleeve and the rod, in which case the shaft is preferably removable from the actuating mechanism with the cutting head.

The actuating mechanism is suitably in a body to which proximal ends of the rod and the sleeve are attached, said attachment being effected by respective locators that are relatively moveable in response to the actuating input. Each locator suitably comprises a collar that receives the sleeve or the rod.

It is preferred that the sleeve and the rod are fixed longitudinally with respect to their respective locators but can be moved angularly with respect to their respective locators. This may be achieved by annular grooves provided on each of the sleeve and the rod, which grooves engage with their respective locators. Preferably, each locator has a pawl that is releasably engageable with the groove, in which case it is advantageous for the pawls of the locators to be operable simultaneously by a single action. For example, a cam may bear on opposed rockers that define the pawls.

The locator of the rod is suitably disposed on the body proximally with respect to the locator of the sleeve and is preferably fixed to the body. The rod may extend proximally beyond its locator to facilitate angular movement of the rod with respect to the body. Conversely, the locator of the sleeve is preferably on a carriage that is movable with respect to the body, such that the actuating input moves the carriage and the sleeve distally with respect to the body. The rocker of the pawl that locates the sleeve may be mounted to the carriage, in which case the aforementioned cam may bear on that rocker when the carriage is in a proximal rest position.

In preferred embodiments, the rod and the sleeve are movable angularly in relation to each other. The range of that relative angular movement may be limited, for example by a pin on the rod that bears against a shoulder on the sleeve, to approximately a quarter turn about the central longitudinal axis of the shaft.

The actuating mechanism suitably includes an actuating element such as a trigger that mounted to the body by a pivot and is suitably biased away from a handgrip. An arm may extend from the trigger beyond the pivot, the arm being engaged with the carriage or with the sleeve to determine the longitudinal position of the sleeve with respect to the body. That arm is preferably floatingly engaged with the carriage or the sleeve; it may have prongs that embrace the sleeve. The sleeve is preferably pivotable with respect to the arm Advantageously, the actuating element is attachable to the body and has a support formation that, when so attached, retains the shaft with respect to the body. It is also possible for the shaft and the body to be assembled by longitudinal insertion of the shaft into the body, followed by lateral displacement of the inserted shaft within the body to retain the shaft with respect to the body.

The invention extends to a cutting head and jaw drive for the instrument of the invention, to a cutting head and shaft for that instrument, and to an actuating mechanism for that instrument.

In order that the invention may be more readily understood, reference will now be made, by way of example, to the accompanying drawings in which:

FIG. 1(a) is an end view of a distal end of a biopsy instrument of the invention, having a shaft supporting a cutting head in an end-cutting configuration;

FIG. 1(b) is a sectional side view on line b-b of FIG. 1;

FIG. 1(c) is a sectional top view on line c-c of FIG. 1;

FIG. 1(d) is a sectional side view corresponding to FIG. 1(b) but showing the jaws of the cutting head splayed apart to disengage them from a sleeve of the shaft;

Figure 4:
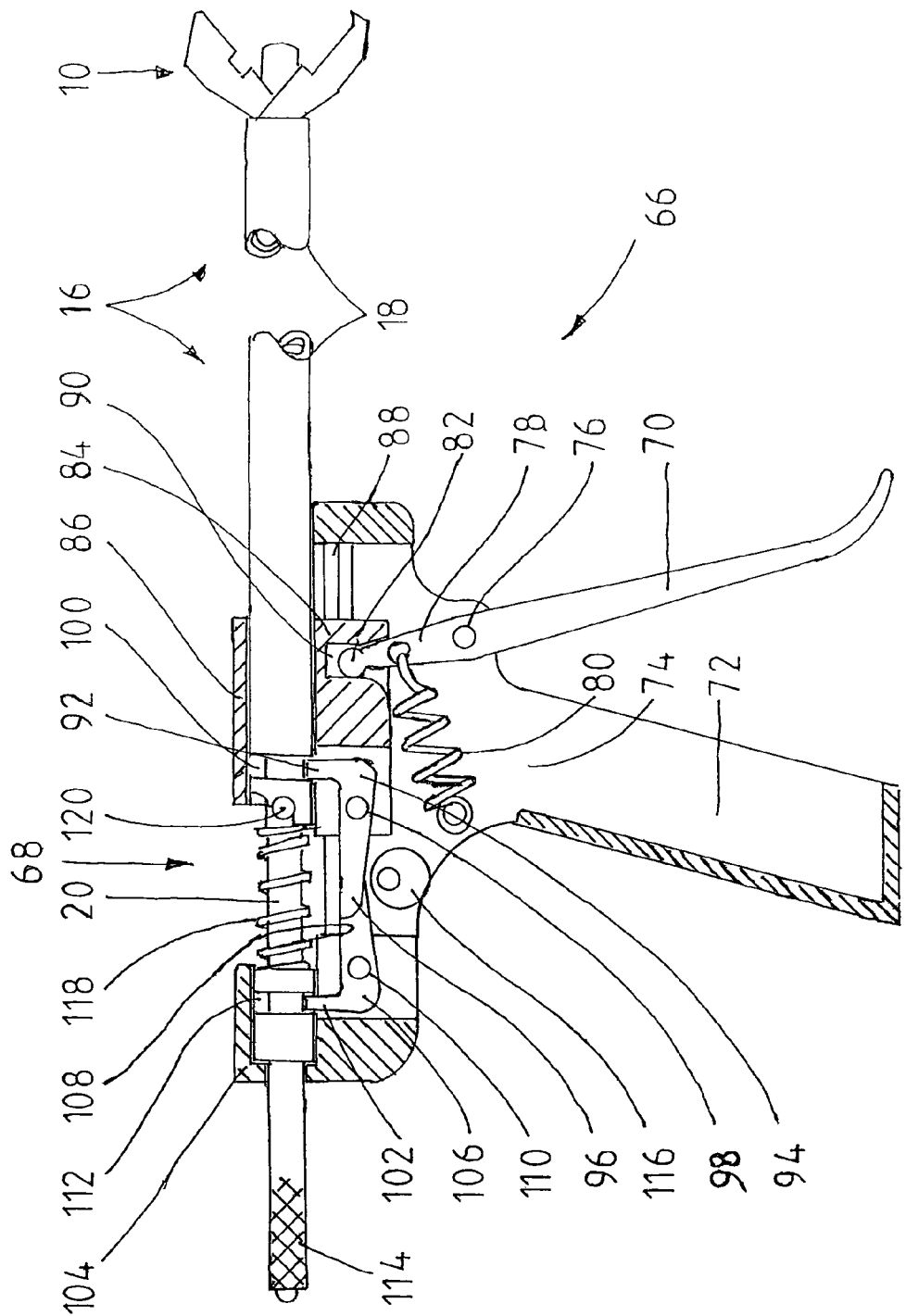
Figure 8A:
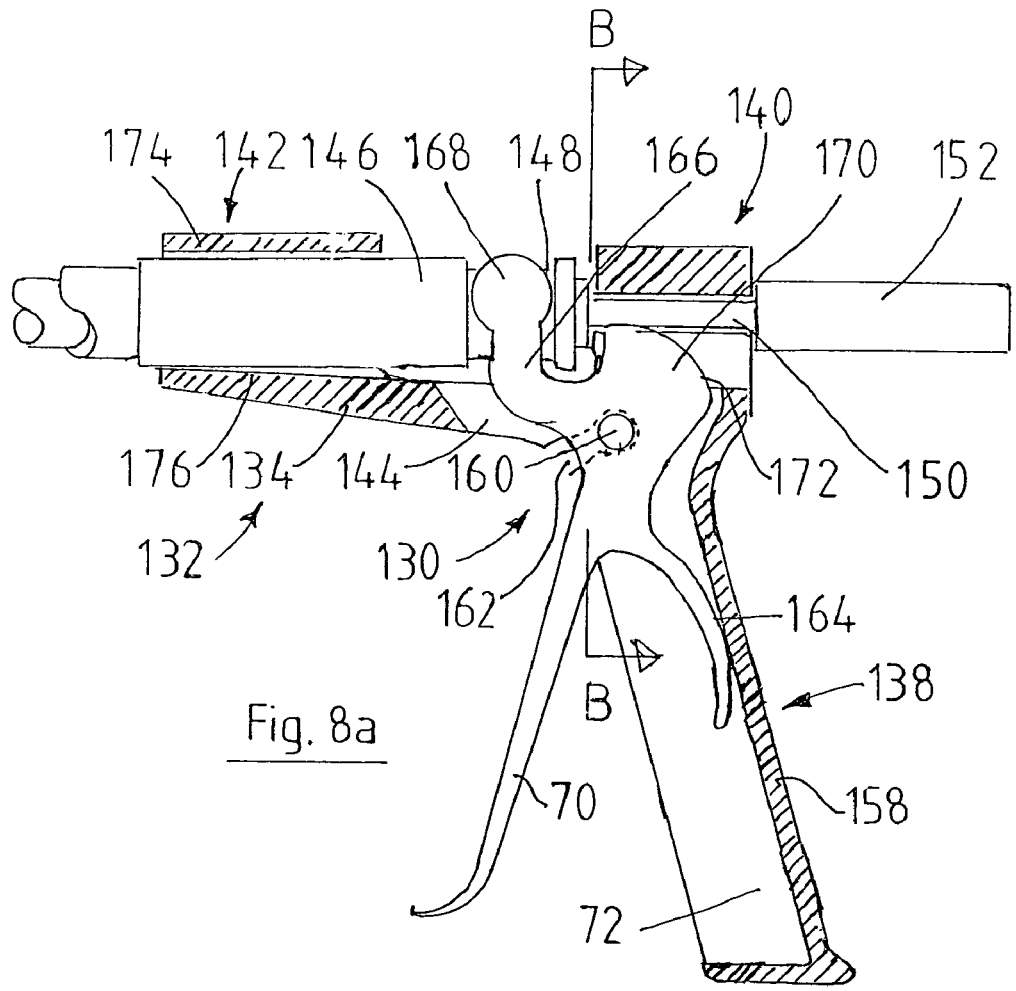
Figure 8B:
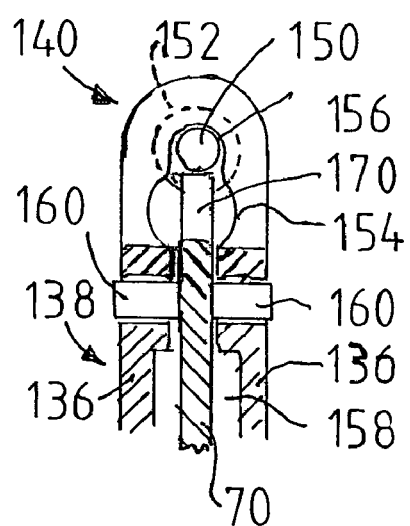

FIGS. 2(a) to 2(f) are sequential sectional side views of a biopsy instrument of the invention taking a biopsy sample from a cervix in which the squamocolumnar junction is remote from the external os, the sequence of drawings showing the movement of the jaws of the cutting head in an end-cutting mode;

FIGS. 3(a) to 3(f) are sequential sectional side views that correspond to FIGS. 2(a) to 2(f) but show the movement of the jaws in a side-cutting mode, taking a biopsy sample from a cervix in which the squamocolumnar junction is close to the external os;

FIG. 4 is a sectional side view of a biopsy instrument in accordance with the invention, having the cutting head and the shaft of the preceding figures removably mounted to a trigger actuating mechanism;

FIG. 5(a) is a side view of a jaw variant that may be moulded with a supporting rod in one piece from plastics;

FIG. 5(b) is a front view of the jaw variant of FIG. 5(a);

FIG. 5(c) is a cross-sectional view of the jaw variant of FIGS. 5(a) and 5(b) taken on line c-c of FIG. 5(a);

FIGS. 6(a) to 6(e) are sequential sectional side views showing the movement of the jaws of FIGS. 5(a) to 5(c) with respect to the sleeve of a shaft in an end-cutting mode;

FIGS. 7(a) to 7(e) are sequential sectional side views showing the movement of the jaws of FIGS. 5(a) to 5(c) with respect to the sleeve of a shaft in a side-cutting mode;

FIG. 8(a) is a sectional side view of a further embodiment of the invention having an actuating mechanism of moulded plastics components; and FIG. 8(b) is a partial sectional view on line b-b of FIG. 8(a).

Referring firstly to FIGS. 1(a) to 1(c) of the drawings, a cutting head 10 comprises first and second co-operable jaws 12, 14. The jaws 12, 14 are at the distal end of a shaft 16 that comprises a circular-section tubular sleeve 18 and a circular-section rod 20 extending through the sleeve 18. The jaws 12,14 are fixed to the distal end of the rod 20 by a pivot 22, and are partly enclosed by the sleeve 18 which is free to move in relation to the rod 20 and the jaws 12,14 to operate the jaws 12,14. Specifically, the pivot 22 supports the jaws 12,14 within a forked end of the rod 20 as best shown in FIG. 1(c).

The first jaw 12 is hollow and at its distal end to define a chamber 24 for receiving and retaining a biopsy sample in use. The open base of the chamber 24 is defined by a peripheral first cutting edge 26. A hole 28 through an outer wall of the first jaw 12 communicates with the interior of the chamber 24 to ease removal of the sample and cleaning of the cutting head 10 after use, if required.

The second jaw 14 has a recess 30 opposed to the chamber 24 of the first jaw 12. The base of the recess 30 serves as a platen against which the first cutting edge 26 of the first jaw 12 bears when the jaws 12,14 close. The recess 30 of the second jaw 14 is surrounded by a peripheral second cutting edge 32 that, when the jaws 12,14 close, receives and surrounds the first cutting edge 26 of the first jaw 12. A hole 34 through an outer wall of the second jaw 14 communicates with the recess 30 to ease cleaning of the cutting head 10 after use, if required. A tooth 36 at the distal tip of the second jaw 14 helps to grip tissue being sampled in use.

Male and female formations 38, 40 in the jaws 12,14 mate as the jaws 12,14 are closed to resist twisting of the jaws 12,14 out of mutual alignment under the cutting forces of use. Correct alignment of the cutting edges 26, 32 is also maintained by the close sliding fit of a flat tongue 42 of the first jaw 12 between parallel cheeks 44 of the second jaw 14. The tongue 42 extends distally from the pivot 22 toward the chamber 24 of the first jaw 12 and the cheeks 44 are defined by a forked part of the second jaw 14 extending distally from the pivot 22 toward the recess 30 of the second jaw 14.

Figure 2A:
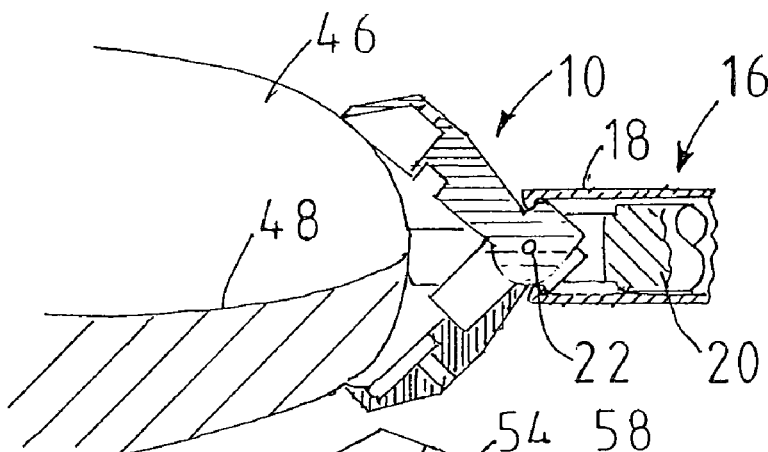

The cutting head 10 is shown in FIGS. 1 (a) to 2(f) and in FIG. 4 in an 'end-cutting' mode, in which the bite direction is aligned with the central longitudinal axis of the shaft 16. As shown in FIG. 2(a) in relation to the anterior lip 46 of the cervix, the end-cutting mode configures the instrument to take tissue samples where the squamocolumnar junction 48 lies remote from the external os, on the front face of the anterior lip 46. The posterior lip has been omitted from FIG. 2(a) but may be expected to have a similarly-positioned squamocolumnar junction. In the end-cutting mode, both jaws 12,14 extend equi-angularly with respect to the central longitudinal axis of the shaft 16 and both jaws 12,14 move through approximately equal angles with respect to that axis to effect a cut.

A distal extension 50 to one side of the sleeve 18 lies clear of the jaws 12,14 in the end-cutting mode, generally aligned with the pivot axis 22. The distal extension 50 comes into play in the side-cutting mode to be described later, whereupon the sleeve 18 is turned about the jaws 12,14 such that the distal extension 50 supports one of the jaws 12,14.

Movement of the jaws 12,14 is determined by interaction between the sleeve 18 and the jaws 12,14 as the sleeve 18 moves with respect to the pivot. In particular, the sleeve 18 has an internal flange 52 at its distal end within which the forked end of the rod 20 is a sliding fit.

Figure 2B:
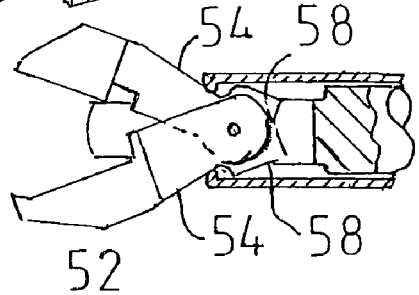

In the end-cutting mode shown, advancing the sleeve 18 distally in relation to the pivot 22 causes the flange 52 to bear on the outer profiles of both of the jaws 12,14, causing the jaws 12,14 to close together and hence to cut the required sample. The sample is then retained in the chamber 24 of the first jaw 12. Advantageously, as shown, the outer profiles of the jaws 12,14 converge proximally to define wedge faces 54 along which the flange 52 slides to impart an increasing closing force upon the jaws 12,14 with increased distal movement of the sleeve 18. The sequence from jaws open to jaws closed is shown in FIGS. 2(a) to 2(c), in which the changing relative positions of the flange 52 and the jaws 12,14 will be noted.

The jaws 12,14 remain closed, retaining the sample in the chamber 24, until the sleeve 18 is returned proximally to its original position in a return stroke, whereupon the jaws 12,14 can move apart to release the sample. In the illustrated embodiment, the internal flange 52 of the proximally-moving sleeve 18 causes the jaws 12,14 to open as shown in FIGS. 2(d) to 2(f), by encountering laterally-projecting proximal lugs 56 of the jaws 12,14. However in other embodiments, it would be possible to move the jaws 12,14 apart by the action of a spring or by the combined effect of a spring and the interaction of the flange 52 with the lugs 56 of the jaws 12,14.

FIG. 1(d) shows how the jaws 12,14 may be splayed apart through substantially 180° to align the projecting lugs 56 so that they can fit into the distal end of the sleeve 18 past the internal flange 52. With the jaws 12,14 splayed in this way, it will be noted that the distal end of the sleeve 18 is bevelled to the same angle as the wedge faces 54 of the jaws 12,14. This allows the jaws 12,14 to be introduced into the sleeve 18 as an assembly with the rod 20.

Figure 2C:
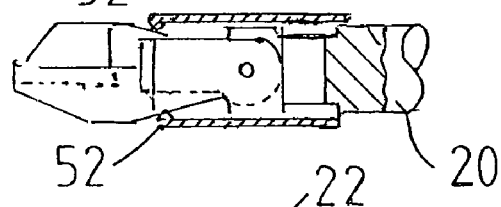
Figure 2D:
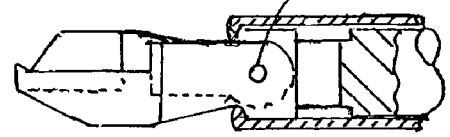
Figure 2E:
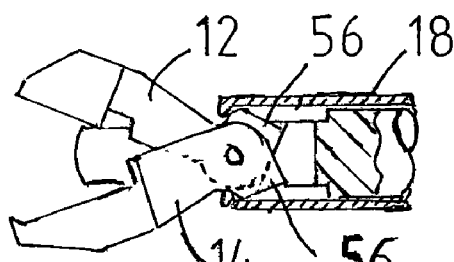
Figure 2F:
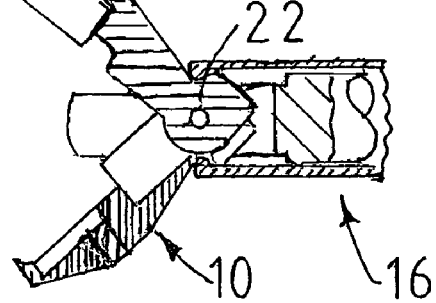

FIGS. 2(c) and 2(d) show that as the jaws 12,14 close, the lugs 56 bear against the inside of the sleeve 18 to hold the pivot 22 on the centre line of the sleeve 18. For this purpose, the lugs 56 have straight outer edges 58 that lie parallel when the jaws 12,14 are closed. Moreover, the spacing between the outer edges 58 of the lugs 56 is slightly less than the internal diameter of the sleeve 18, allowing clearance for the sleeve 18 to move relative to the lugs 56 and for the lugs 56 to pivot within the sleeve 18. Provided that sufficient clearance is maintained from the pivot 22 to allow the jaws 12,14 to open and close, proximal parts of the rod 20 may be thicker to fit the full internal diameter of the sleeve 18 and hence to maintain the central alignment of the rod 20.

Moving on now to FIGS. 3(a) to 3(f), this shows the instrument configured in a side-cutting mode adapted to take tissue samples from a squamocolumnar junction 48 that lies in the most common position close to the external os 60, on the inwardly-facing portion of the surrounding convex annular lip 46 of the cervix. This situation is shown particularly in FIG. 3(a) where the inward location of the squamocolumnar junction 48 may be contrasted with the situation in FIG. 2(a). The bite direction is therefore offset from the central longitudinal axis of the shaft 16 as shown. In the side-cutting mode, the second jaw 14 remains stationary, substantially aligned with the central longitudinal axis of the shaft 16 and the first jaw 12 closes against it to effect a cut.

Figure 3A:
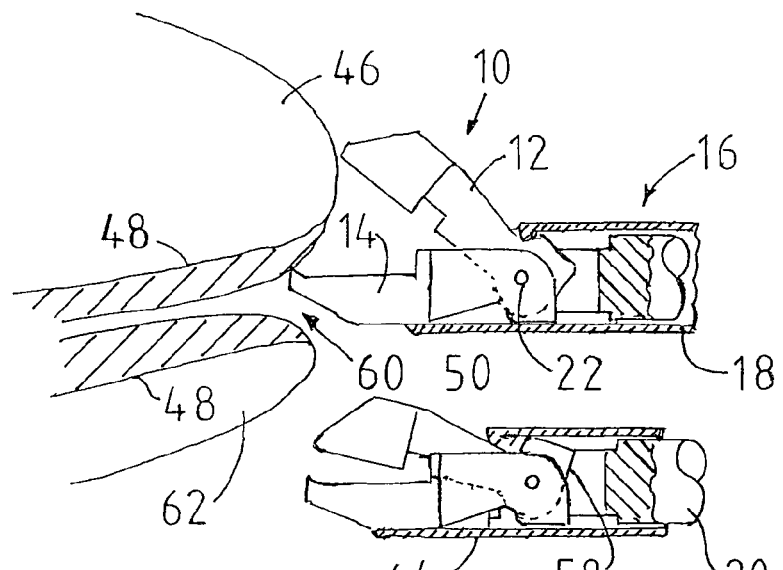
Figure 3B:
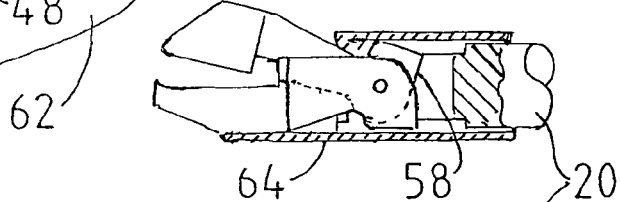
Figure 3C:
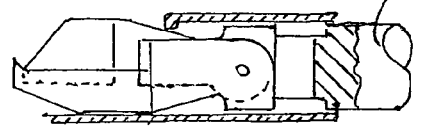
Figure 3D:
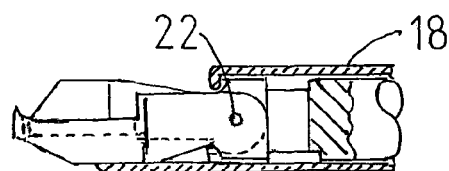
Figure 3E:
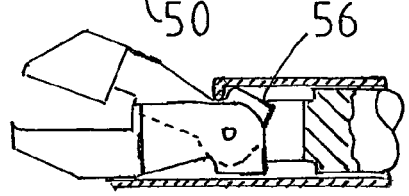
Figure 3F:
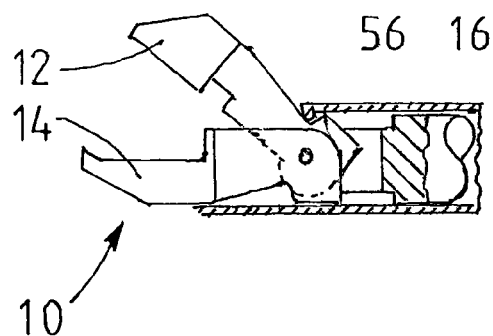

The longitudinal displacement between the jaws 12,14 at the start of the cut should be noted: this allows the stationary second jaw 14 to enter the cervical canal through the external os 60 between the anterior and posterior lips 46, 62 of the cervix as shown in FIG. 3(a). The instrument is shown here sampling from the anterior lip 46 but could also be turned around to sample from the posterior lip 62. This may be achieved by turning the rod 20 and the sleeve 18 together about the central longitudinal axis of the shaft 16 with respect to the actuating mechanism shown in FIG. 4.

Reconfiguring the cutting head 10 into the side-cutting mode involves disengaging the second jaw 14 from interaction with the sleeve 18 and supporting the second jaw 14 to hold it stationary while the first jaw 12 moves during a cutting action.

The second jaw 14 may be disengaged from interaction with the sleeve 18 by virtue of the flange 52 of the sleeve 18 being interrupted around part of its circumference. The interruption defines a gap 64 in the flange 52 of sufficient width that when the gap 64 and the second jaw 14 are mutually aligned, the sleeve 18 can pass over the second jaw 14, without interaction, as the sleeve 18 moves distally and proximally with respect to the pivot 22.

When reconfiguring the cutting head 10 from the end-cutting mode into the side-cutting mode, the gap 64 and the second jaw 14 may be mutually aligned simply by turning the sleeve 18 through 90° about the rod 20 and about the jaws 12,14 attached to the rod 20. It is equally possible to turn the rod 20, and the jaws 12,14 attached to the rod 20, through 90° within the sleeve 18. This relative angular movement of the rod 20 and the sleeve 18 also brings into play the aforementioned distal extension 50 of the sleeve 18, which extends around less than one quarter of the circumference of the sleeve 18 but is of sufficient width to support the second jaw 14 extending parallel to the central longitudinal axis of the shaft 16.

Thus in the side-cutting mode, relative angular movement between the sleeve 18 and the rod 20 brings the distal extension 50 of the sleeve 18 into supporting relation with the second jaw 14, with that jaw 14 being supported parallel to the sleeve 18 and being aligned with the gap 64 in the internal flange 52 of the sleeve 18. Consequently, in this mode the second jaw 14 does not move, remaining parallel with the sleeve 18 as the sleeve 18 advances and retracts distally and proximally, and the cutting movement is performed by the first jaw 12 to give a bite direction offset from the central longitudinal axis of the shaft 16.

Moving now to FIG. 4 of the drawings, a biopsy instrument 66 comprises the shaft 16 and the cutting head 10 of the preceding figures. The cutting head 10 is at the distal end of the elongate shaft 16 and an actuating mechanism 68 is at the proximal end of the shaft 16. The actuating mechanism 68 is operatively connected to the cutting head 10 by the rod 20 and the sleeve 18 that together constitute the shaft 16, whereby a physician may operate the cutting head 10 in use by causing relative movement between the sleeve 18 and the rod 20.

The jaws 12,14 of the cutting head 10 are normally biased open but close in response to the physician squeezing a trigger 70 toward a handgrip 72 of the actuating mechanism 68. This advances the sleeve 18 distally relative to the rod 20, whereupon the sleeve 18 bears upon the jaws 12,14 to close them as described above. When the trigger 70 is released, the sleeve 18 retracts proximally with respect to the rod 20, permitting (indeed, in the embodiment described above, causing) the jaws 12,14 to open.

In the embodiment shown in FIG. 4, the shaft 16 and the cutting head 10 can be removed from the actuating mechanism 68 whereby the shaft 16 and the cutting head 10 can be discarded after use and the actuating mechanism 68 can be reused with a fresh disposable shaft 16 and cutting head 10. It is possible for the shaft 16 and the cutting head 10 to be largely of plastics material for inexpensive disposal and for the actuating mechanism 68 to have metal components for long life. Disposability of at least part of the instrument 66 is not essential but is much preferred. Of course, if the actuating mechanism 68 is also disposable and particularly if it is of single-use design, then the issue of longevity does not arise.

The handgrip 72 of the actuating mechanism 68 is integral with a hollow body 74 and is swept back proximally and downwardly from the body 74 in pistol-like fashion. The trigger 70 of the actuating mechanism 68 lies distally ahead of the handgrip 72 and is attached to the body by a pivot 76 close to where the handgrip 72 extends into the body 74.

An arm 78 extending integrally from the trigger 70 beyond the pivot 76 is connected to the body 74 by a tension spring 80 that biases the arm 78 proximally, and hence the pivoting trigger 70 distally, against the actuating pressure of a physician's fingers in use. The arm 78 terminates in an end joint 82 that is pivotally engaged with a carriage 84 movably mounted to the body 74, whereby the carriage 84 is moved by the movement of the trigger 70 and hence of the arm 78, transmitted through the end joint 82. The carriage 84 supports the sleeve 18 of the shaft 16 received within a tubular collar 86 atop the carriage 84. The carriage 84 is mounted in internal grooves 88 in opposed side walls of the body 74 for sliding movement with respect to the body 74, parallel to the central longitudinal axis of the shaft 16. It will be noted that the end joint 82 of the arm 78 floats in a recess 90 in the underside of the carriage 84 to avoid a geometric clash between the arcuate movement of the arm 78 and the straight sliding movement of the carriage 84.

The sliding movement of the carriage 84 with respect to the body 74 moves the sleeve 18 to operate the jaws 12,14. Thus, the sleeve 18 moves distally when the trigger 70 is squeezed and moves proximally under the tension of the spring 80 acting on the arm 78 when the trigger 70 is released.

The sleeve 18 is removably attached to the carriage 84 by a spring-loaded retainer pawl 92 acting within the tubular collar 86 atop the carriage 84. The pawl 92 is part of a generally L-shaped rocker 94 that includes a cam follower 96 opposed to the pawl 92 about a hinge 98 that attaches the rocker 94 to the carriage 84. A spring (not shown) associated with the hinge 98 biases the pawl 92 toward the sleeve 18, whereby the pawl 92 engages an annular groove 100 in a locating formation on the sleeve 18. This arrangement effects positive longitudinal location of the sleeve 18 with respect to the carriage 84 but allows the sleeve 18 to be turned with respect to the carriage 84 about the central longitudinal axis of the sleeve 18.

Similarly, the rod 20 of the shaft 16 is removably attached to the body 74 by a second spring-loaded retainer pawl 102 acting within a tubular collar 104 atop the proximal end of the body 74 that receives the rod 20. Again, the pawl 102 is part of a generally L-shaped rocker 106 that includes a cam follower 108 opposed to the pawl 102 about a hinge 110, but in this instance the hinge 110 attaches the rocker 106 to the body 74. The pawl 102 is biased toward the sleeve 18 by a spring (not shown) associated with the hinge 110, whereby the pawl 102 engages an annular groove 112 in a locating formation on the rod 20 to effect positive longitudinal location of the rod 20 with respect to the body 74.

The locating formation of the rod 20 anchors the rod 20 to the body 74 when the sleeve 18 is moved, and prevents the sleeve 18 being withdrawn so far as to allow the jaws 12,14 to disengage from the internal flange of the sleeve 18.

Again, the longitudinal location afforded by the groove 112 allows the rod 20 to be turned with respect to the body 74 about the central longitudinal axis of the rod 20. This allows the jaws 12,14 of the cutting head 10 to be turned about the central longitudinal axis of the shaft 16, optimizing the plane of cut in relation to the position of the handgrip 72 and thus the hand position of a physician using the instrument 66. The rod 20 has a knurled proximal end 114 to facilitate that turning movement, and also to hold the rod 20 while turning the sleeve 18 about the rod 20 to change the cutting mode.

A cam 116 is pivotally attached to the body 74 to operate the retainer pawls 92, 102 associated with the rockers 94, 106. An external lever (not shown) on a side wall of the body 74 may be used to turn the cam 116. The rockers 94, 106 operate in opposite angular senses such that the cam followers 96, 108 of the rockers 94, 106 overlap when the carriage 84 is in its proximal position, whereby the single cam 116 acts simultaneously upon both of the cam followers 96, 108.

When the cam 116 is in the state shown in FIG. 4, the cam followers 96, 108 swing toward the pivot axis of the cam 116 under the spring loading of the rockers 94, 106, allowing the pawls 92, 102 to engage the respective grooves 100, 112 of the shaft 16 and of the rod 20. When the cam 116 is turned through 180° with the carriage 84 in its proximal position at rest, the cam 116 bears against the cam followers 96, 108 to push them away from the pivot axis of the cam 116, turning the rockers 94, 106 about their hinges 98, 110 against spring bias to disengage the pawls 92, 102 from their associated grooves 100, 112. The sleeve 18 may then be removed from the carriage 84 and the rod 20 may be removed from the body 74 to disassemble the instrument 66 for replacement of the cutting head 10 and shaft 16.

The rod 20 extends within a compression spring 118 acting between the locating formations of the rod 20 and the sleeve 18. This spring 118 biases the sleeve 18 distally with respect to the rod 20 to keep the jaws 12,14 closed.

The actuating mechanism 68 provides for rapid and secure loading of the disposable part of the instrument 66 and for simple and positive transition between the two cutting modes by relative angular movement between the sleeve 18 and the rod 20. Relative angular movement between the sleeve 18 and the rod 20 is limited to a quarter turn by a pin 120 projecting from the rod 20 that bears against shoulders spaced by 90° on the proximal end of the sleeve 18.

Many variations are possible within the inventive concept. One such variation is shown in FIGS. 5(a) to 7(e). This shows a flexibly-hinged plastics moulding combining the jaws 12,14 and the rod 20 in a single component for reduced cost, with a design that is simple to mould. Thin flexible leaves 122 extend outwardly from the distal end of the rod 20 and terminate in first and second jaws 12,14 akin to those of the preceding embodiment. FIGS. 5(a) to 5(c) show the component as moulded whereas FIGS. 6(a) to 7(e) show the component in use.

The leaves 122 of the as-moulded component of FIGS. 5(a) to 5(c) are bent into opposed semi-circular shapes until a spigot 124 on one of the leaves inward of the second jaw 14 snap-fits into a correspondingly-positioned hole 126 in the other leaf inward of the first jaw 12, as shown in FIGS. 6(a) to 7(e). This holds the jaws 12,14 together before the moulded component is introduced into the sleeve 18, and creates a fulcrum about which the jaws 12,14 hinge by deformation of the thicker leaf portions 128 between the fulcrum and the jaws 12,14. As the semi-circular leaves 122 co-operate to form a circular loop whose external diameter substantially matches the internal diameter of the sleeve 18, the fulcrum is held centrally within the sleeve 18 despite the cutting forces experienced in use.

Figure 6A:
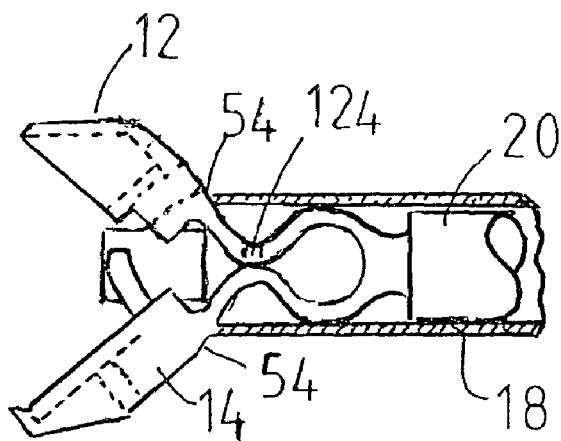
Figure 6B:
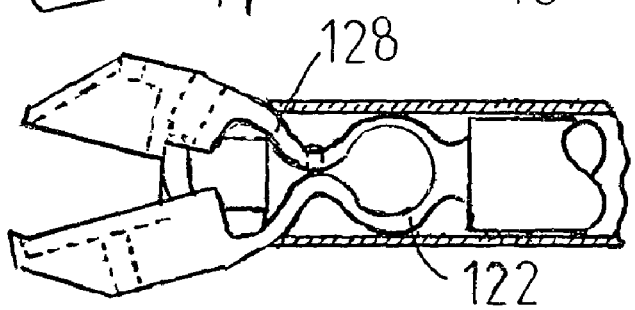
Figure 6C:
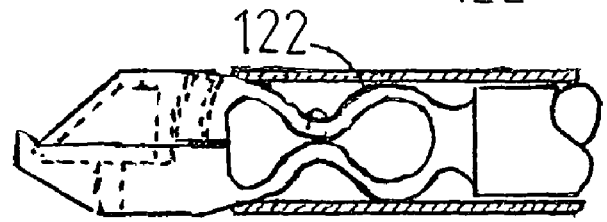
Figure 6D:
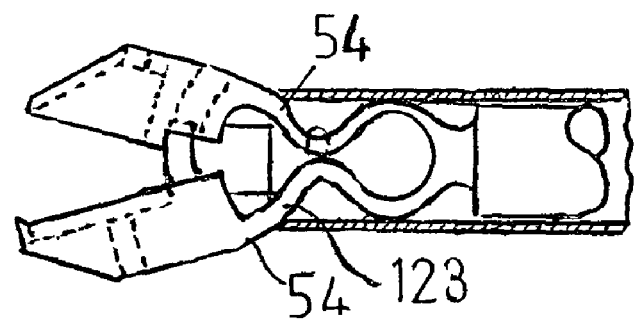
Figure 6E:
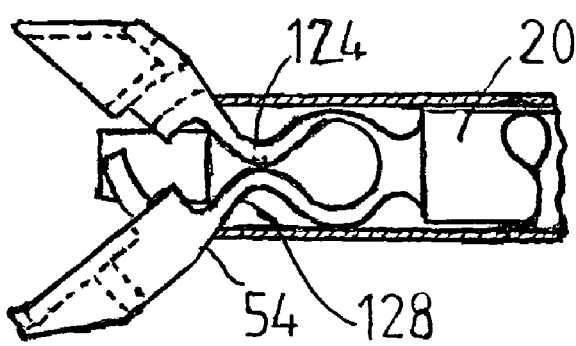

In use, the distally-advancing sleeve 18 bears on wedge faces 54 of the jaws 12,14 as in the preceding embodiment to close the jaws 12,14 and to cut a tissue sample. These movements are shown in FIGS. 6(a) to 6(c) for the end-cutting mode and in FIGS. 7(a) to 7(c) for the side-cutting mode. As the sleeve 18 moves proximally to its original position in a return stroke, the resilience of the thicker leaf portions 128 opens the jaws 12,14 for retrieval of the cut sample. These movements are shown in FIGS. 6(c) to 6(e) for the end-cutting mode and in FIGS. 7(c) to 7(e) for the side-cutting mode. So, there is no need in this embodiment for the inwardly-directed flange at the distal end of the sleeve 18 that is a feature of the preceding embodiment.

As in the preceding embodiment, male and female formations 38, 40 associated with the jaws 12,14 engage with each other as the jaws 12,14 close to keep the jaws 12,14 in alignment. These formations are a curved projection 38 of one jaw 14 that fits within a curved channel 40 of the other jaw 12, the curvature of the projection 38 and of the channel 40 being determined by their radius from the fulcrum defined by the spigot 124 engaged in the hole 126.

Turning finally to FIGS. 8(a) and 8(b), these show how an actuating mechanism may be made wholly or largely of plastics components to create a single-use embodiment that is wholly disposable.

The actuating mechanism 130 of the instrument 132 shown in FIGS. 8(a) and 8(b) includes an injection-moulded plastics body 134 defined by spaced parallel generally planar side walls 136 braced by various cross-walls and other transverse formations. The body 134 has three main elements: a downwardly-extending hollow proximal handgrip 138; a proximal locator collar 140 atop the handgrip 138; and a generally tubular guide 142 disposed distally with respect to the collar 140. The guide 142 is spaced from the collar 140 by a chamber 144 extending downwardly through the body 134 between the side walls 136, which chamber 144 extends into the hollow interior of the handgrip 138. Whilst preferably moulded in one piece, the body 134 could instead be moulded in two pieces joined by welding or bonding along a central longitudinal plane.

As previously, a shaft 16 of the instrument comprises a rod 20 supported by the collar 140, which rod 20 extends distally within a sleeve 18 that is movable with respect to the rod 20. However in this embodiment of the invention, the sleeve 18 is mounted for longitudinal movement relative to the guide 142, in addition to being pivotable within the guide 142 about the central longitudinal axis of the shaft 16. For this purpose, the sleeve 18 has a bearing portion 146 of increased thickness at its proximal end that is coincident with and extends beyond the guide 142. An annular proximal groove 148 encircles the bearing portion 146 of the sleeve 18.

A cutting head, not shown in FIGS. 8(a) and 8(b), lies at the distal end of the shaft 16, with the jaws 12,14 of the cutting head being moulded integrally with the rod 20 as described above in relation to FIGS. 5(a) to 7(e). The jaws 12,14 are closed by distal movement of the sleeve 18 relative to the rod 20, as before, for which purpose the bearing portion 146 of the sleeve 18 slides distally within the guide 142.

The rod 20 has a bearing portion 150 of reduced thickness coincident with the collar 140, inward of the proximal end of the rod 20. This leaves a proximal end portion 152 of the rod 20 extending proximally beyond the collar 140, whereby the rod 20 can be turned readily about its central longitudinal axis within the collar 140. This adjusts the plane of the jaws 12,14 relative to the body 134 of the instrument 132, in similar manner to the embodiment of FIG. 4.

As best appreciated in FIG. 8(b), the collar 140 has a longitudinal internal channel of keyhole cross section, comprising a relatively wide lower leg 154 and a relatively narrow upper leg 156. The narrow upper leg 156 of the channel has a central longitudinal axis aligned with the central longitudinal axis of the shaft 16 when mounted for use as shown, and has a diameter that fits closely around the thin bearing portion 150 of the rod 20. Thus, the narrow upper leg 156 of the channel is of a length, width and depth that snugly accommodates the bearing portion 150 of the rod 20. Conversely, the wider lower leg 154 of the channel is wide enough to admit the proximal end portion 152 of the rod 20 during assembly of the instrument 132 as will be explained. Also, the lower leg 154 of the channel is open-bottomed and communicates with the chamber 144 of the body 134 and with the hollow interior of the handgrip 138 below.

The handgrip 138 is swept proximally and downwardly in pistol-grip fashion as in the embodiment of FIG. 4. However, in this instance, the handgrip 138 is open-fronted, having a proximal wall 158 between the two side walls 136 but no distal wall.

An injection-moulded trigger 70 disposed distally with respect to the handgrip 158 has laterally-extending trunnions 160 that snap-fit into pivotal engagement with distally-opening slots 162, one in each side wall 136 of the body 134 at the top of the handgrip 138. A leaf spring 164 integrally moulded with the trigger 70 is cantilevered to the proximal side of the trigger 70, where it fits between the side walls 136 within the handgrip 138. The spring 164 bears against the proximal wall 158 of the handgrip 138 to bias the trigger 70 distally against the actuating pressure of a physician's fingers in use.

The chamber 144 of the body 134 accommodates a forked curved arm that extends integrally from the trigger 70 beyond the trunnions. The arm has spaced parallel prongs 166, only one of which is visible in the side view of FIG. 8(a). Each prong 166 curves distally and then upwardly as shown before terminating in a rounded end 168. The rounded ends 168 of the prongs 166 embrace and engage with the annular groove 148 on the enlarged bearing portion 146 of the sleeve 18. Pivotal floating movement of the rounded ends 168 within the annular groove 148 converts pivotal movement of the trigger 70, and hence of the arm, into longitudinal movement of the sleeve 18 within and with respect to the guide 142.

A support 170 moulded integrally with the trigger 70 lies proximally with respect to the arm between the side walls 136 of the body 134, under the collar 140 that holds the rod 20. The support 170 extends through the open bottom of the wider lower leg 154 of the keyhole-section channel within the collar 140. Here, the upper surface of the support 170 bears against and supports the underside of the bearing portion 150 of the rod 20, confining that portion 150 of the rod 20 in the narrower upper leg 156 of the keyhole-section channel. The support 170 has a curved upper surface 172 whose substantially constant radius of curvature intersects the pivot axis of the trunnions 160, thereby ensuring that the support 170 performs its function throughout the stroke of the trigger 70, keeping the rod 20 in position in the upper leg 156 of the keyhole-section channel.

The guide 142 has a distally-tapering longitudinal bore that is substantially coaxial with the upper leg 156 of the keyhole-section channel in the collar 140. More specifically, the upper inner wall 174 of the bore is parallel to the central longitudinal axis of the shaft 16 and is spaced from that axis by half the diameter of the sleeve 18. Thus, when the support 170 confines the rod 20 to the upper leg 156 of the keyhole-section channel in the collar 140, the rod 20 in turn holds the sleeve 18 against the upper inner wall 174 of the bore of the guide 142. Conversely the lower inner wall 176 of the bore is inclined slightly away from the central longitudinal axis of the shaft 16 moving proximally from the distal opening of the guide 142. This creates lateral clearance in the proximal end of the guide 142 to permit angular movement of the shaft 16 relative to the body 134 about a transverse axis, enabling assembly of the shaft 16 and trigger 70 into the body 134 as will now be described.

Firstly, the moulding defining the jaws 12,14 and the rod 20 is inserted into the sleeve 18 to create a shaft assembly. Then, the proximal end of the shaft assembly is inserted through the distal opening of the guide 142, with the proximal end of the rod 20 leading the proximal end of the sleeve 18 into and through the guide 142. In so doing, the shaft assembly is tilted slightly with respect to the body 134 to slide along the inclined lower inner wall 176 of the guide 142. This aims the proximal end of the rod 20 into and through the wide lower leg 154 of the keyhole-section channel in the collar 140.

The shaft 16 assembly is fed into the guide 142 until the proximal end of the rod 20 protrudes from the proximal end of the keyhole-section channel in the collar 140. At this stage, with the thin bearing portion 150 of the rod 20 aligned with the narrow upper leg 156 of the keyhole-section channel in the collar 140, the shaft assembly may be pivoted about a transverse axis until the bearing portion 150 of the rod 20 engages into the upper leg 156 of the channel.

When the trunnions 160 of the trigger 70 are then snap-fitted into the slots 162 in the handgrip 138, the support 170 that is integral with the trigger 70 enters the lower leg 156 of the keyhole-section channel in the collar 140 to retain the bearing portion of the rod 20 in the narrow upper leg 156 of the channel. Simultaneously, the rounded ends 168 of the prongs 166 defining the arm that is integral with the trigger 70 engage with the annular slot 148 in the bearing portion 146 of the sleeve 18. The leaf spring 164 also bears against the proximal wall 158 of the handgrip 138 to brace the instrument 132, biasing the trigger 70 distally and the sleeve 18 proximally. Proximal movement of the trigger 70 against this bias results in the sleeve 18 moving distally to close the jaws 12,14. Conversely, the bias moves the trigger 70 distally upon release, which movement causes the sleeve 18 to retreat proximally allowing the jaws 12,14 to open in view of their resilient mounting to the rod 20.

Attaching the trigger 70 to the body 134 in this way results in effectively permanent assembly of all the parts, as the rod 20 cannot then be moved longitudinally relative to the body 134 without first disengaging the trunnions 160 from the slots 162 so that the support 170 can be moved clear of the rod 20. Nevertheless, the cutting mode may still be changed by relative pivotal movement between the rod 20 and the sleeve 18 about the central longitudinal axis of the rod 20. Similarly, the rod 20 and the sleeve 18 may be turned together to allow the plane of cut to be varied relative to the body of the instrument and hence in relation to a physician's hand.

It is not essential that all of the components of a disposable instrument are of plastics, particularly if stronger and cheaper solutions may be implemented in metal. For example, the sleeve 18 could be an extruded metal tube.

The invention claimed is:
1. A biopsy instrument comprising:
a support;
a cutting head having first and second co-operable jaws movable with respect to the support between open and closed states; and
a jaw drive for moving one or both of the jaws into the closed state to take a biopsy sample in response to an actuating input from a user;
wherein the jaw drive is user-adjustable between first and second cutting modes differentiated by the bite direction of the jaws with respect to a central longitudinal axis of the instrument, the bite direction being the centerline between the open jaws, wherein, in the first cutting mode, the bite direction is substantially aligned with the central longitudinal axis of the instrument and in the second cutting mode, the bite direction is substantially offset from the central longitudinal axis of the instrument; and
wherein the user-adjustable jaw drive comprises a sleeve movable distally with respect to the support to bear against at least one of the jaws, thereby to drive the closing movement of that jaw between the open and closed states, the sleeve having a jaw-supporting formation that is disengaged from the jaws in the first cutting mode to allow both jaws to move relative to the support, and that is engaged with one of the jaws in the second cutting mode to restrain the movement of that jaw relative to the support.

2. The instrument of claim 1, wherein the support is a rod extending proximally from the cutting head.

3. The instrument of claim 1, wherein the jaws are hinged to the support.

4. The instrument of claim 3, wherein the jaws are attached to the support by a pivot.

5. The instrument of claim 3, wherein the jaws are integrally formed with the support via resilient leaves.

6. The instrument of claim 5, wherein the leaves are bent to define a fulcrum and a locating formation that centers the fulcrum with respect to a central longitudinal axis of the instrument.

7. The instrument of claim 6, wherein the leaves are attached to each other at the fulcrum.

8. The instrument of claim 1 wherein, in the first cutting mode, both jaws move with respect to the support between the open and closed states.

9. The instrument of claim 8 wherein, in the first cutting mode, both jaws move substantially equi-angularly with respect to the support.

10. The instrument of claim 1 wherein, in the second cutting mode, one jaw moves more than the other jaw with respect to the support between the open and closed states.

11. The instrument of claim 10 wherein, in the second cutting mode, one jaw remains substantially stationary with respect to the support and the other jaw moves between the open and closed states.

12. The instrument of claim 1, wherein each jaw has a proximally-tapering wedge face against which the sleeve bears when driving closing movement of that jaw between the open and closed states.

13. The instrument of claim 1, wherein the sleeve has an inwardly-extending flange that, when moving distally, bears against at least one of the jaws to drive closing movement of that jaw between the open and closed states.

14. The instrument of claim 13, wherein each jaw has a proximal lug and the flange of the sleeve bears against the lug of at least one of the jaws when moving proximally with respect to the support in a return stroke, the flange thereby driving opening movement of that jaw between the closed and open states.

15. The instrument of claim 14, wherein when the jaws are closed, their proximal lugs co-operate to define outwardly-facing parallel flat faces that lie parallel to the inner wall of the sleeve to centre the support within the sleeve.

16. The instrument of claim 13, wherein adjustment between the first and second cutting modes is effected by relative angular movement between the sleeve and the support, and wherein the flange of the sleeve is interrupted by a gap that is brought into alignment with one of the jaws in the second cutting mode.

17. The instrument of claim 1, wherein the jaw-supporting formation is a distal extension of the sleeve extending partially around the circumference of the sleeve.

18. The instrument of claim 1, wherein adjustment between the first and second cutting modes is effected by relative angular movement between the sleeve and the support, and wherein the jaw-supporting formation is brought into alignment with one of the jaws in the second cutting mode.

19. The instrument of claim 1, wherein the jaws have opposed co-operable alignment formations that mate with each other as the jaws close.

20. The instrument of claim 1, wherein one jaw has a flat tongue that slides between parallel cheeks of the other jaw.

21. The instrument of claim 1, wherein the jaws are biased to assume the open state when released by the jaw drive.

22. The instrument of claim 1, wherein the actuating input is provided by an actuating mechanism at a proximal end of the instrument.

23. The instrument of claim 22, wherein the cutting head is connected to the actuating mechanism by a shaft.

24. The instrument of claim 23, wherein the shaft implements the support and the jaw drive.

25. The instrument of claim 24, wherein
the shaft comprises the sleeve.

26. The instrument of claim 25, wherein:
the support is a rod extending proximally from the cutting head; and
the shaft comprises the rod and the rod is within the sleeve.

27. The instrument of claim 26, wherein the actuating mechanism is in a body that supports proximal ends of the rod and the sleeve.

28. The instrument of claim 27, wherein the actuating input acts directly upon the sleeve to move the sleeve distally with respect to the body.

29. The instrument of claim 27, wherein the rod and the sleeve are attached to the body by respective locators.

30. The instrument of claim 28, wherein at least one of the sleeve and/or the rod can be moved angularly with respect to their respective locators.

31. The instrument of claim 29, wherein the rod and the sleeve are movable angularly in relation to each other.

32. The instrument of claim 30, wherein the range of said relative angular movement is limited.

33. The instrument of claim 31, wherein a pin on the rod bears against a shoulder on the sleeve to limit said range.

34. The instrument of claim 31, wherein the range of said relative angular movement is limited to approximately a quarter turn about the central longitudinal axis of the shaft.

35. The instrument of claim 29, wherein at least one of the sleeve and/or the rod are fixed longitudinally with respect to their respective locators.

36. The instrument of claim 35, wherein the sleeve and the rod are fixed longitudinally with respect to their respective locators and the actuating input causes relative movement between the locators.

37. The instrument of claim 35, wherein an annular groove provided on each of the sleeve and the rod engages with their respective locators.

38. The instrument of claim 29, wherein each locator comprises a collar that receives the sleeve or the rod.

39. The instrument of claim 38, wherein the locator of the sleeve is a guide in which the sleeve can be moved longitudinally relative to the body.

40. The instrument of claim 29, wherein the locator of the rod is disposed on the body proximally with respect to the locator of the sleeve.

41. The instrument of claim 29, wherein the rod extends proximally beyond its locator to facilitate angular movement of the rod with respect to the body.

42. The instrument of claim 29, wherein the locator of the rod is fixed to the body.

43. The instrument of claim 29, wherein the locator of the sleeve is on a carriage that is movable with respect to the body.

44. The instrument of claim 43, wherein the actuating input moves the carriage and the sleeve distally with respect to the body.

45. The instrument of claim 44, wherein the actuating mechanism has a user-movable actuating element acting upon the carriage or upon the sleeve.

46. The instrument of claim 45, wherein the actuating element is attachable to the body and has a support formation that, when so attached, retains the shaft with respect to the body.

47. The instrument of claim 45, wherein the actuating element is a trigger.

48. The instrument of claim 47, wherein the trigger is biased away from a handgrip.

49. The instrument of claim 47, wherein the trigger is mounted to the body by a pivot and an arm extends from the trigger beyond the pivot, the arm being engaged with the carriage or the sleeve to determine the longitudinal position of the sleeve with respect to the body.

50. The instrument of claim 49, wherein the arm is floatingly engaged with the carriage or the sleeve.

51. The instrument of claim 49, wherein the arm has prongs that embrace the sleeve.

52. The instrument of claim 49, wherein the sleeve is pivotable with respect to the arm.

53. The instrument of claim 22, wherein the cutting head is removable from the actuating mechanism such that the actuating mechanism can be re-used with a fresh cutting head.

54. The instrument of claim 53, wherein:
the cutting head is connected to the actuating mechanism by a shaft; and the shaft is removable from the actuating mechanism with the cutting head.

55. The instrument of claim 54, wherein:
the shaft comprises a sleeve and a rod within the sleeve, the rod extending proximally from the cutting head and defining the support;
the actuating mechanism is in a body that supports proximal ends of the rod and the sleeve;
the rod and the sleeve are attached to the body by respective locators, at least one of the rod and/or the sleeve being fixed longitudinally with respect to their respective locators; an annular groove provided on each of the sleeve and the rod engages with their respective locators; and
each locator has a pawl that is releasably engageable with the groove.

56. The instrument of claim 55, wherein the pawls of the locators are operable simultaneously by a single action.

57. The instrument of claim 56, wherein a cam bears on opposed rockers that define the pawls.

58. In combination, a cutting head and jaw drive for use in a biopsy instrument comprising:

a support;

a cutting head having first and second co-operable jaws movable with respect to the support between open and closed states; and a jaw drive for moving one or both of the jaws into the closed state to take a biopsy sample in response to an actuating input from a user;

wherein the jaw drive is user-adjustable between first and second cutting modes differentiated by the bite direction of the jaws with respect to a central longitudinal axis of the instrument, the bite direction being the centerline between the open jaws, wherein, in the first cutting mode, the bite direction is substantially aligned with the central longitudinal axis of the instrument and in the second cutting mode, the bite direction is substantially offset from the central longitudinal axis of the instrument;

wherein the user-adjustable jaw drive comprises a sleeve movable distally with respect to the support to bear against at least one of the jaws, thereby to drive the closing movement of that law between the open and closed states; and wherein the cutting head and jaw drive are removable from an actuating mechanism such that the actuating mechanism can be reused with a fresh cutting head and jaw drive.

59. In combination, a cutting head and shaft for use in a biopsy instrument comprising:

a support;

a cutting head having first and second co-operable jaws movable with respect to the support between open and closed states; and a jaw drive for moving one or both of the jaws into the closed state to take a biopsy sample in response to an actuating input from a user;

wherein the jaw drive is user-adjustable between first and second cutting modes differentiated by the bite direction of the jaws with respect to a central longitudinal axis of the instrument, the bite direction being the centerline between the open jaws, wherein, in the first cutting mode, the bite direction is substantially aligned with the central longitudinal axis of the instrument and in the second cutting mode, the bite direction is substantially offset from the central longitudinal axis of the instrument;

wherein the user-adjustable jaw drive comprises a sleeve movable distally with respect to the support to bear against at least one of the jaws, thereby to drive the closing movement of that law between the open and closed states; and wherein the cutting head and shaft are removable from an actuating mechanism such that the actuating mechanism can be reused with a fresh cutting head and shaft.

60. An actuating mechanism for providing an actuating input in a biopsy instrument, the instrument comprising:

a support;

a cutting head having first and second co-operable jaws movable with respect to the support between open and closed states; and a user-adjustable jaw drive for moving one or both of the jaws into the closed state to take a biopsy sample in response to the actuating input;

wherein the user-adjustable jaw drive comprises a sleeve movable distally with respect to the support to bear against at least one of the jaws, thereby to drive closing movement of that jaw between the open and closed states; and wherein the cutting head is connected to the actuating mechanism by a shaft, the shaft implementing the support and the jaw drive, and the actuating mechanism.

* * * * *

UNITED STATES PATENT AND TRADEMARK OFFICE
CERTIFICATE OF CORRECTION

| | |
|---|---|
| PATENT NO. | : 8,096,956 B2 |
| APPLICATION NO. | : 12/440348 |
| DATED | : January 17, 2012 |
| INVENTOR(S) | : George et al. |

It is certified that error appears in the above-identified patent and that said Letters Patent is hereby corrected as shown below:

Col. 17, Line 21, Claim 58, "that law" should read --that jaw--;

Col. 18, Line 13, Claim 59, "that law" should read --that jaw--.

Signed and Sealed this
Tenth Day of July, 2012

David J. Kappos
*Director of the United States Patent and Trademark Office*